US012582548B2

(12) United States Patent
Sakakibara et al.

(10) Patent No.: US 12,582,548 B2
(45) Date of Patent: Mar. 24, 2026

(54) IN VIVO TEMPERATURE CONTROL SYSTEM

(71) Applicant: Toray Industries, Inc., Tokyo (JP)

(72) Inventors: Hajime Sakakibara, Otsu (JP); Tatsufumi Nomura, Tokyo (JP); Hiroki Nakajima, Otsu (JP); Akinori Matsukuma, Otsu (JP); Jun Mikami, Otsu (JP)

(73) Assignee: Toray Industries, Inc., Tokyo (JP)

( * ) Notice: Subject to any disclaimer, the term of this patent is extended or adjusted under 35 U.S.C. 154(b) by 301 days.

(21) Appl. No.: 18/284,326

(22) PCT Filed: Mar. 31, 2022

(86) PCT No.: PCT/JP2022/016464
§ 371 (c)(1),
(2) Date: Sep. 27, 2023

(87) PCT Pub. No.: WO2022/211011
PCT Pub. Date: Oct. 6, 2022

(65) Prior Publication Data
US 2024/0148547 A1      May 9, 2024

(30) Foreign Application Priority Data

Mar. 31, 2021    (JP) ................................. 2021-059750

(51) Int. Cl.
*A61F 7/12* (2006.01)
*A61F 7/00* (2006.01)

(52) U.S. Cl.
CPC ............ *A61F 7/123* (2013.01); *A61F 7/0085* (2013.01); *A61F 2007/0056* (2013.01); *A61F 2007/0091* (2013.01)

(58) Field of Classification Search
CPC ....... A61F 7/12; A61F 7/123; A61F 2007/126
See application file for complete search history.

(56) References Cited

U.S. PATENT DOCUMENTS 10,105,178 B2    10/2018  Calabro' et al.
2003/0199747 A1   10/2003  Michlitsch et al.
(Continued)

FOREIGN PATENT DOCUMENTS

EP        3679976 A1    7/2020
EP        4049602 A1    8/2022
(Continued)

OTHER PUBLICATIONS

Extended European Search Report dated Feb. 24, 2025, from counterpart European Application No. 22781221.1.
(Continued)

*Primary Examiner* — Kaitlyn E Smith
(74) *Attorney, Agent, or Firm* — DLA Piper LLP (US)

(57) ABSTRACT

An in vivo temperature control system includes a catheter insertable into a biological lumen; two or more temperature sensors placed such that they can measure a temperature distribution in a longitudinal direction of the biological lumen; a liquid storage section that stores a liquid; and a control section that estimates a spatial change in the biological lumen based on a temperature change before and after the liquid in the liquid storage section is released outwardly through the catheter, wherein the temperature change is measured by each of two or more temperature sensors.

5 Claims, 3 Drawing Sheets

(56)         References Cited

U.S. PATENT DOCUMENTS

| | | |
|---|---|---|
| 2004/0002749 A1 | 1/2004 | Joye et al. |
| 2004/0116988 A1* | 6/2004 | Hammack ................. A61F 7/12 |
| | | 607/105 |
| 2005/0090735 A1 | 4/2005 | Carney et al. |
| 2010/0087782 A1 | 4/2010 | Ghaffari et al. |
| 2011/0196255 A1 | 8/2011 | Kassab |
| 2013/0211282 A1 | 8/2013 | Bunch |
| 2016/0249969 A1 | 9/2016 | Santoinanni et al. |
| 2019/0183560 A1* | 6/2019 | Ballakur ................... A61F 7/12 |

FOREIGN PATENT DOCUMENTS

| | | |
|---|---|---|
| JP | 2006-521878 A | 9/2006 |
| JP | 2012-505041 A | 3/2012 |
| JP | 2016-534777 A | 11/2016 |
| JP | 2019-080783 A | 5/2019 |
| JP | 6618254 B2 | 12/2019 |
| JP | 6804910 B2 | 12/2020 |

OTHER PUBLICATIONS

International Search Report dated Jun. 21, 2022 in counterpart International Application No. PCT/JP2022/016464 w/English translation.
Written Opinion dated Jun. 21, 2022 in counterpart International Application No. PCT/JP2022/016464.

\* cited by examiner

IN VIVO TEMPERATURE CONTROL SYSTEM

TECHNICAL FIELD

This disclosure relates to an in vivo temperature control system capable of estimating a spatial change in a biological lumen.

BACKGROUND

Atrial fibrillation is a kind of arrhythmia, and known to involve repeated irregular contraction of the atrium, leading to poor blood circulation, hence causing discomfort or malaise. Therefore, methods of treating atrial fibrillation have been widely carried out by catheter ablation procedures, wherein the pulmonary vein and the cardiac muscle tissues in the vicinity thereof such as the posterior wall of the left atrium, which are major sources of occurrence of atrial fibrillation, are ablated (pulmonary vein isolation).

On the other hand, since the site of ablation (left atrium) and the esophagus are positioned close to each other during the treatment by a catheter ablation procedure, it has been pointed out that there is a risk of injury of the esophagus, leading to severe esophageal complications such as left atrial-esophageal fistula and esophagus vagus nerve paralysis. Thus, appropriate control of the temperature in the esophagus is required.

Examples of means for the control of the temperature in the esophagus that have been reported include a temperature measurement device that employs an approach through the nose or mouth of the patient (nasal or oral approach) to insert a catheter equipped with a temperature sensor into the esophagus. The temperature sensor measures the internal esophageal temperature, and an alert is output to the outside when the internal temperature is judged to have reached a threshold (JP 6618254 B).

A device that calculates the remaining time until the internal esophageal temperature reaches the temperature limit based on the temperature change rate of the internal esophageal temperature and outputs it to the outside has also been reported (JP 6804910 B).

An esophageal catheter system comprising first and second expansion members in contact with the esophageal wall, wherein a liquid is injected between the expansion members to control the internal esophageal temperature has also been reported (JP 2019-80783 A).

To appropriately control the internal esophageal temperature during the treatment by a catheter ablation procedure, it is required that the internal esophageal temperature be continuously monitored, and proactive measures be taken before the intraesophageal tissue are damaged.

The temperature measurement device described in JP '254 is capable of monitoring the internal esophageal temperature during the ablation therapy and outputting the alert to the outside when the internal temperature is judged to have reached a threshold, to thereby allow one to take prior measures such as stopping of the ablation before the esophagus is injured by heating or cooling. However, the esophagus temperature may be rapidly changed during ablation therapy, and thus a delay in noticing of the alert may lead to a delay in the required measures.

The device described in JP '910 can calculate the time until the temperature reaches a dangerous temperature at which the esophagus is damaged based on the rate of change of the internal esophageal temperature and output it to the outside, to thereby allow for prediction of rapid temperature changes of the esophagus temperature and time to take required care. However, since the device does not have a mechanism for controlling the internal esophageal temperature within safe temperatures, the risk of esophagus damage cannot be reduced when the measures are delayed.

The esophageal temperature controlling system described in JP '783 can appropriately control the internal esophageal temperature by making a space between the two expansion members and injecting a liquid to the space in the esophagus while plugging. However, the pressure of the ablation catheter on the cardiac muscle tissue can easily cause the lumen of the adjacent esophagus to be in a narrowed or obstructed state, resulting in failure of distribution of the injected fluid throughout the lumen and difficulty in controlling the internal esophageal temperature.

Accordingly, it could be helpful to provide an in vivo temperature control system that can monitor the internal temperature of a biological organ such as esophagus, and detect spatial changes in a biological lumen based on the measurement of the temperature distribution in the longitudinal direction in the biological lumen in time sequence by injection of a liquid.

SUMMARY

We thus provide:

(1) An in vivo temperature control system comprising:
    a catheter insertable into a biological lumen;
    two or more temperature sensors placed such that they can measure a temperature distribution in a longitudinal direction of the biological lumen;
    a liquid storage section that stores a liquid; and
    a control section that estimates a spatial change in the biological lumen based on a temperature change before and after the liquid in the liquid storage section is released outwardly through the catheter;
    wherein the temperature change is measured by each of the two or more temperature sensors.

(2) The in vivo temperature control system of (1), comprising a monitor that displays the signal detected from the temperature sensor, as a visual information,
    wherein the monitor has a means that allows an operator to know the spatial change in a biological lumen.

(3) The in vivo temperature control system of (1) or (2), wherein the spatial change is narrowed state or obstructed state of the biological lumen.

(4) The in vivo temperature control system of (3), comprising an alert output section that outputs an alert to the outside when the biological lumen is judged to be in a narrowed state or obstructed state.

(5) The in vivo temperature control system of (3) or (4), wherein, in estimating the spatial change in the biological lumen, the control section judges the biological lumen to be not in a narrowed state or obstructed state when temperature changes larger than a preset threshold are detected by all the two or more temperature sensors.

(6) The in vivo temperature control system of (3) or (4), wherein, in estimating the spatial change in the biological lumen, the control section judges the biological lumen to be in a narrowed state or obstructed state based on the temperature changes in the longitudinal direction of the biological lumen detected by the two or more temperature sensors, wherein a temperature change smaller than a preset threshold is detected by any one of the temperature sensors, and temperature changes larger than the preset threshold are detected by all the temperature sensors positioned downstream, in the direction of the flow of the liquid, of the temperature sensor that detects the temperature change smaller than the threshold.

Thus, the internal temperature of the biological lumen can be measured by the temperature sensor and adjusted to a predetermined temperature using a liquid, and a spatial change in a biological lumen can be detected by measuring temperature changes in the longitudinal direction in the biological lumen by liquid injection.

DESCRIPTION OF SYMBOLS

Figure 1:
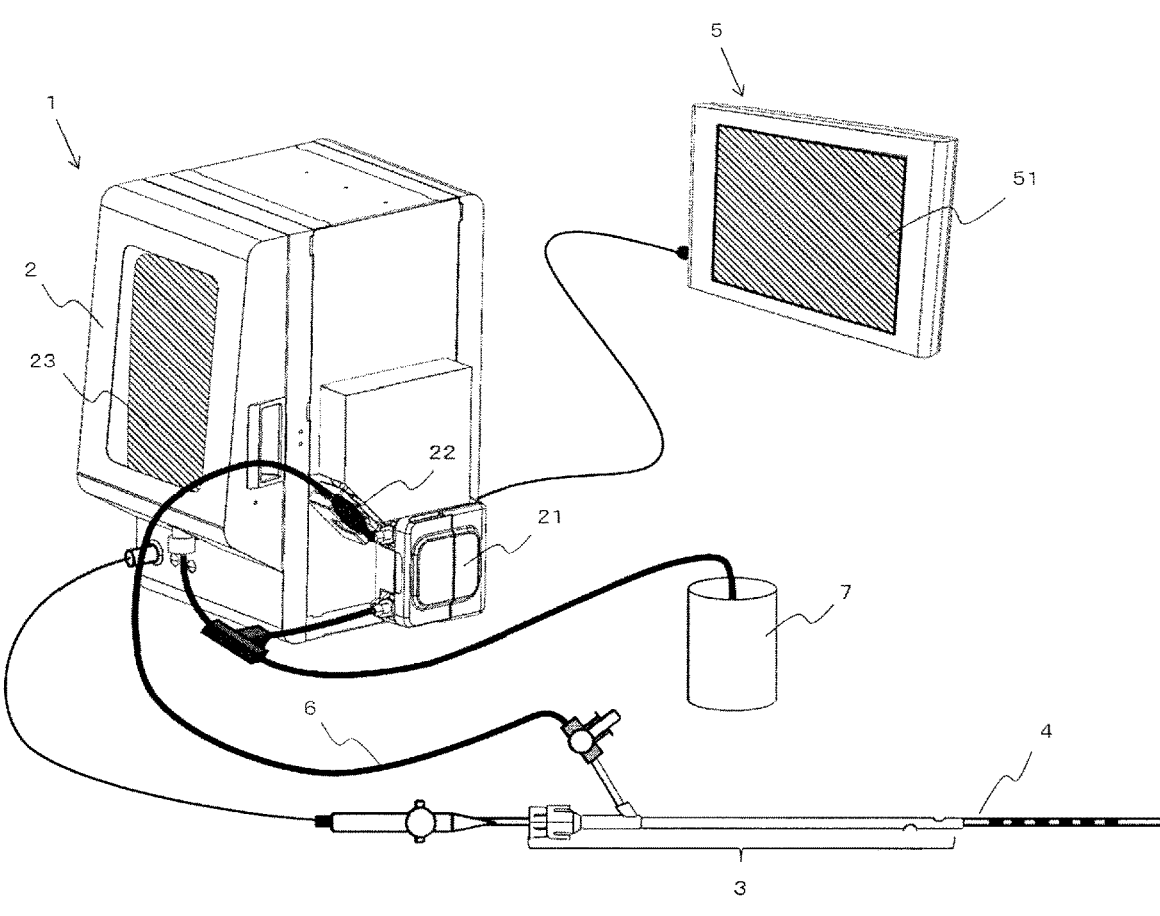
FIG. 1 is diagram illustrating the external appearance of an in vivo temperature control system according to a first example.

1: in vivo temperature control system, 2: in vivo temperature control device, 3: catheter, 4: temperature probe, 5: monitor, 6: liquid-sending-sucking dual-purpose tube, 7: waste liquid section, 21: pump, 22: pressure sensor, 23: liquid storage section, 24: control section, 31: tube section, 32: valved connector, 41: shaft section, 42: temperature sensor, 43: handle section, 44: connection cable, 51: touch-screen display, 61: bulge section, 62: channel switching section, 63: liquid supply port, 64: connection port, 71: esophagus, 72: cardiac muscle tissue, 73: liquid, 221: contact-type displacement gauge, 231: Peltier device, 321: port, 322: valve, 431: connector, 621: three-way check valve, 631: needle

DETAILED DESCRIPTION

Specific examples of our systems are described below with reference to drawings. However, this disclosure is not limited to the examples. Our systems may be modified as appropriate without departing from the scope in which the desired effect can be produced. The same reference numerals are used for the same components.

First Example

FIG. 1 is a diagram illustrating the external appearance of an in vivo temperature control system 1 according to a first example. For example, when an ablation procedure is carried out using a balloon ablation catheter in which the inside of the balloon is heated using a radiofrequency, the in vivo temperature control system 1 may be used to monitor the internal esophageal temperature in a position close to the heart to be treated by the ablation, and also to cool the internal esophageal temperature with a liquid. The biological organ to which the in vivo temperature control system 1 is applicable is not limited. The system may be applied to the pharynx, larynx, lung, esophagus, stomach or the like. It is especially preferably used for cooling of the inside of the esophagus.

The in vivo temperature control system 1 herein comprises: an in vivo temperature control device 2 that sends or sucks a temperature-controlled liquid to or from a catheter 3; a catheter 3 on which a pore(s) through which a liquid can be sent into or sucked from the outside is/are formed, the catheter being insertable into the living body; a temperature probe 4 containing two or more temperature sensors 42 placed such that they can measure the temperature distribution in the longitudinal direction of the biological lumen, the probe being insertable into the catheter 3; a monitor 5 capable of displaying a signal from the temperature probe 4; a liquid-sending-sucking dual-purpose tube 6 connected to a pump 21 and a pressure center 22, the tube connecting the in vivo temperature control device 2 to the catheter 3; and a waste liquid section 7.

Figure 2:
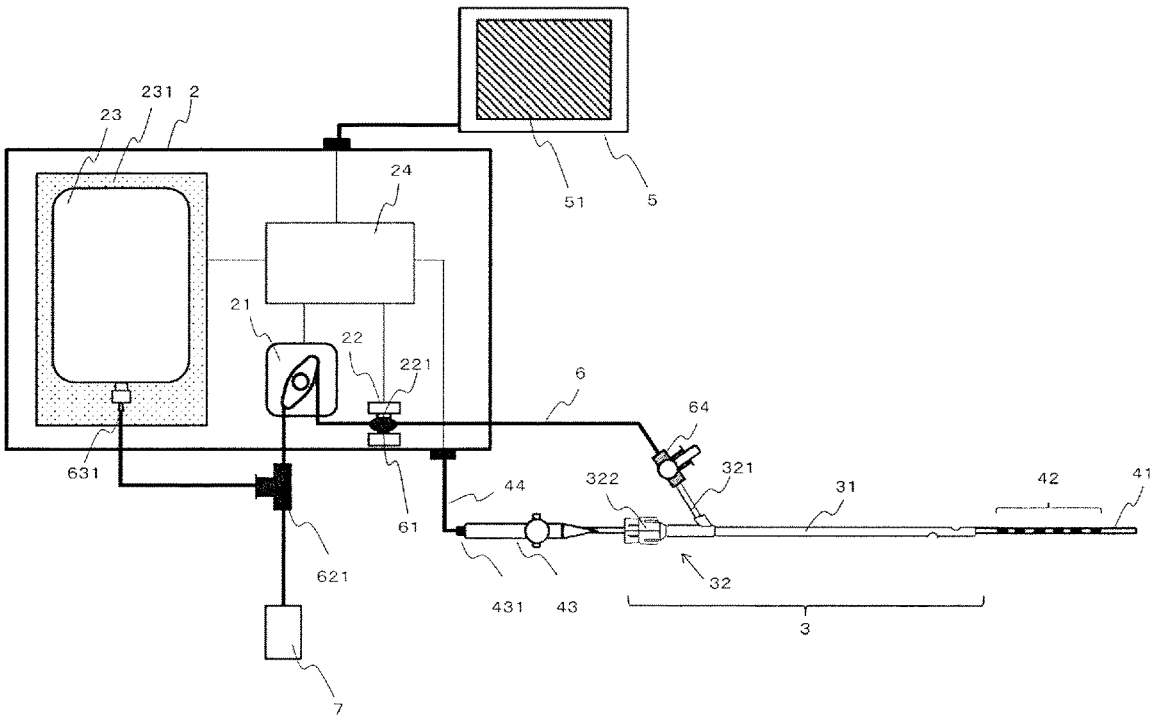
FIG. 2 is a schematic diagram illustrating the internal structure of the in vivo temperature control system illustrated in FIG. 1.

FIG. 2 is a schematic diagram illustrating the internal structure of the in vivo temperature control device 2 illustrated in FIG. 1.

The in vivo temperature control device 2 comprises: a pump 21 that sends or sucks a liquid to or from the catheter 3; a pressure sensor 22 that sends the internal pressure of the catheter 3; a liquid storage section 23 that stores the temperature-controlled liquid; and a control section 24 that controls the driving of the pump based on a signal detected from the temperature probe 4 or a signal detected from the pressure sensor 22.

The pump 21 contained in the in vivo temperature control device 2 is a roller-type tube pump. By the forward rotation of the roller of the pump 21, a liquid can be sent from the liquid storage section 23 to the catheter 3. By the reverse rotation of the roller of the pump 21, a liquid can be sucked from the distal end portion or the pore(s) of the catheter 3.

The liquid storage section 23 of the in vivo temperature control system 1 of the first example is a general, commercially available infusion bag for physiological saline, glucose solution or the like. The liquid storage section 23 has a structure by which it can be housed inside the in vivo temperature control device 2. In the in vivo temperature control device 2, a Peltier device 231 and an in-device temperature sensor, which is not shown, for measurement of the temperature in the liquid storage section 23 are placed such that they are in contact with the liquid storage section 23. By controlling the temperature of the Peltier device 231 based on a signal detected from the in-device temperature sensor, temperature control of the liquid stored in the liquid storage section 23 can be carried out. When a catheter ablation procedure using a hot balloon is carried out, the temperature of the liquid in the liquid storage section 23 is controlled preferably at 0° C. to 15° C., more preferably at 0° C. to 10° C.

The liquid storage section 23 may be in any shape as long as it is capable of storing a liquid such as physiological saline. The liquid storage section 23 may be housed inside the in vivo temperature control device 2, or may be placed outside the in vivo temperature control device 2. When the liquid storage section 23 is housed inside the in vivo temperature control device 2, it is preferred that temperature control of the liquid in the liquid storage section 23 can be made as described above. In an example other than the first example, the infusion bag may be cooled using a coolant such as ice instead of the Peltier device 231, or an infusion bag that has been preliminarily frozen may be used while thawing it. The liquid used may be purified water or tap water instead of the physiological saline or glucose solution.

When used in cryoablation that requires the inside of the living body to be warmed to a higher level than usual, the in vivo temperature control system may be used therefor. In such instances, the liquid stored in the liquid storage section 23 may be heated to a temperature of 30° C. to 45° C. using a heating resistor.

The control section 24 included in the in vivo temperature control device 2 detects a signal(s) (such as the thermoelectromotive force) from the temperature sensor(s) 42 in the temperature probe 4 connected to the in vivo temperature control device 2, and then converts the signal(s) to temperature information (in vivo temperature(s)).

The control section 24 controls the pump 21. It drives the pump 21 based on a signal detected from the temperature probe 4 or a sending command by operating the monitor 5, such that the liquid in the liquid storage section 23 is released to the outside through the catheter 3. Further, the control section 24 contained in the in vivo temperature control device 2 preferably comprises a circuit for controlling the driving of the pump 21 based on a signal detected by the pressure sensor 22. For example, the control section 24 of the in vivo temperature control system 1 according to the first example has a mechanism that allows numerical conversion of the information from the liquid-sending-sucking dual-purpose tube 6 on the amount of displacement to pressure information.

The control section 24 also comprises a circuit for estimating a spatial change in the biological lumen (for example, narrowed state or obstructed state in the lumen) based on temperature changes in the two or more temperature sensors 42 placed in the longitudinal direction of the biological lumen before and after release of the liquid into the biological lumen. Specifically, whether or not a liquid can smoothly flow down from upstream to downstream, in other words, whether or not the inside of the biological lumen is in a narrowed state or obstructed state is estimated based on the temperature changes measured by the two or more temperature sensors placed in the longitudinal direction in the biological lumen. In this example, whether the plurality of the temperature sensors 42 placed in the longitudinal direction is positioned upstream or downstream in the liquid flow direction can be preferably preset in the control section 24. Alternatively, the control section 24 may judge whether the temperature sensors 42 are positioned upstream or downstream in the liquid flow direction based on the temperature shift by the temperature sensors 42 detecting the temperature changes when a liquid is allowed to flow down from upstream to downstream. In the in vivo temperature control system in the first example, the controller that drives the pump 21 and the circuit that estimates a spatial change in a biological lumen are carried out by the same control section 24. However, no limitation is made to this example, and a configuration in which separate control sections are prepared for control, or a configuration separately having a controller means via the internet may be included.

Further, the control section 24 preferably comprises a circuit that controls the internal temperature of the liquid storage section 23 based on a signal detected from the in-device temperature sensor for measurement of the temperature inside the liquid storage section 23.

The in vivo temperature control device 2 also comprises an alert output section that is not shown, and the control section 24 also has a control function that outputs a predetermined alert (e.g., voice) from an alert output section when it judges that a predetermined conditions are satisfied. Specifically, when the biological lumen is judged to be in a narrowed state or obstructed state, the control section 24 outputs an alarm command to the alert output section, and allows the alert output section to generate a voice alert. In the in vivo temperature control system in the first example, the controller for the pump 21 and the circuit that outputs a command generating an alert to the alert output section are carried out by the same control section 24. However, no limitation is made to this example, and a configuration in which separate control sections are prepared for control, or a configuration separately having a controller via the internet may be included.

The catheter 3 is a cylindrical member insertable into a living body by a nasal or oral approach, and capable of sending or sucking a liquid through the distal end of the catheter or a pore(s) formed on the surface, through a lumen. More specifically, the catheter 3 has a structure comprising a tube section 31 insertable into a living body, and a valved connector 32 fixed at the proximal end side in the longitudinal direction of the tube section 31.

The material used for the tube section 31 is not limited as long as it is a flexible material nasally or orally insertable into a living body, and examples of the material include thermoplastic resins such as polyvinyl chloride, polyurethane, and silicone. For the confirmation of the site of placement in the living body, the material preferably contains a radiopaque material.

For example, when the tube section 31 is nasally inserted into the living body from the nose, the length of the tube section 31 is preferably about 200 mm to 1000 mm; the outer diameter is preferably about 1.7 mm to 6.0 mm; and the inner diameter is preferably about 1.0 mm to 5.0 mm.

The valved connector 32 is fixed at the proximal end side of the tube section 31, and connectable to the liquid-sending-sucking dual-purpose tube 6. The valved connector 32 comprises a port 321 for sending or sucking of the liquid from the distal end side of the tube section 31, and a valve 322 for fixing the temperature probe 4 when the temperature probe 4 is inserted to the catheter 3. The valve 322 is preferably openable and closable by a rotational motion or the like. The above configuration enables manipulation of the temperature probe 4 when the valve 322 is open, and enables fixation of the temperature probe 4 when the valve 322 is closed.

The temperature probe 4 is a member used to be nasally or orally inserted into a living body and measure the internal temperature of a biological lumen. The temperature probe 4 comprises a shaft section 41 to be inserted into the living body, two or more temperature sensors 42 placed on the temperature probe such that they can measure the temperature distribution in the longitudinal direction of the biological lumen, and a handle section 43.

The material used for the shaft section 41 is not limited as long as it is a flexible material nasally or orally insertable into a living body, and examples of the material include thermoplastic resins such as polyether block amide, polyurethane, nylon, polyolefin, polyamide, and polyetherpolyamide.

The outer diameter of the shaft section 41 is preferably about 1.0 mm to 4.0 mm, more preferably a diameter that allows insertion of the shaft section 41 into a lumen of the catheter 3. The shaft section 41 preferably has a length of about 300 mm to 1100 mm. When it is inserted into a lumen of the catheter 3, the temperature sensor 42 on the shaft section 41 is preferably placed at a position where it protrudes from the distal end side of the catheter 3.

The shaft section 41 may have a function by which the distal end side can be deflected by operation of the handle section 43. By this, in particular, in an application to the esophagus, the risk of straying into the airway can be reduced when the temperature probe 4 is nasally or orally inserted into the esophagus. Moreover, the esophagus is meandering, rather than being straight, between the pharynx and the gastric cardia. By the deflection operation, placement of the temperature sensor 42 at a desired esophageal site is possible.

The temperature sensors 42 may be placed in any arrangement as long as they can measure the temperature distribution in the longitudinal direction of the biological lumen. When the temperature sensors 42 are placed on the temperature probe 4, they are preferably placed at the distal end. The number of the temperature sensors 42 contained is two or more, and is preferably three or more to measure the temperature distribution in the longitudinal direction in the biological lumen in time sequence and detect a spatial change more accurately.

The material used for the temperature sensor 42 is not limited as long as it has good thermal conductivity. It is preferably a radiopaque material from the viewpoint of measurement of the temperature at a position close to the ablation site.

The handle section 43 comprises a connector 431 for connection to the in vivo temperature control device 2. In the in vivo temperature control system 1 according to the first example, the in vivo temperature control device 2 is connected to the temperature probe 4 through a connection cable 44.

In the first example, the catheter 3 for releasing a liquid to the outside and the temperature probe 4 in which temperature sensors 42 are placed are independent, and are configured such that the temperature probe 4 is inserted into the catheter 3. In another example, temperature sensors may be placed on the tube section of the catheter 3. In this example, a pore(s) through which a liquid can be sent into a living body is/are preferably placed at the proximal end side in the longitudinal direction of each temperature sensors placed on the catheter 3.

The monitor 5 is capable of displaying information on the internal temperature in the living body detected by the temperature probe 4, as visual information such as a digital number, bar graph, and trend graph. The monitor 5 has a function by which, when the temperature in the biological organ has exceeded a preset threshold, the display color is changed to present the temperature change to an operator as visual information.

The monitor 5 also has a means for allowing an operator to know the spatial change in a biological lumen, and when a spatial change occurs in the biological lumen, can visually inform the operator that the inside of the biological lumen is in a narrowed state or obstructed state. By this, for example, the operator can early recognize that the inside of the esophagus is in a narrowed state or obstructed state during treatment of arrhythmia by a catheter ablation procedure so that the pressure can be released and the ablation source moved away from the esophagus to reduce the risk of esophageal injury. In addition, as a result of the recognition by the operator that the inside of the esophagus is in a narrowed state or obstructed state, the operator can manipulate the ablation catheter such that a narrowed state or obstructed state inside the esophagus does not occur, which allows the liquid to smoothly flow down from upstream to downstream so that the temperature control in the esophagus using a liquid can be effectively performed.

The monitor 5 preferably has a transmitter that transmits to the operator information on the operation of sending and sucking of the liquid; information on errors that have occurred in the system, and alerts including alarms; and operational information such as the operation time, the numbers of times of sending and sucking of the liquid, and the amount of liquid sent. By this, the operational conditions, malfunctioning conditions, and dangerous conditions can be informed to the operator not only by a visual means but also by an aural means.

The monitor 5 preferably comprises a touch-screen display 51 with which various parameters related to the system operation can be input, and with which the input parameters can be transmitted to the control section 24 of the in vivo temperature control device 2. This enables the operator to start and stop the operation, and to set and modify various parameters, of the in vivo temperature control device 2 from a distant location.

The monitor 5 can also transmit a signal to the control section 24 of the in vivo temperature control device 2 to allow injection and suction of a liquid to be performed regardless of the internal temperature of the biological lumen. By this, the operator can send a driving command for injection and suction of a liquid at any timing.

The liquid-sending-sucking dual-purpose tube 6 is a tube for delivering a liquid from the liquid storage section 23 to the catheter 3 through the pump 21 during the sending of the liquid, and delivering a liquid from the catheter 3 to the waste liquid section 7 during the suction of the liquid. The waste liquid section 7 is a site for storing the unnecessary liquid after the suction of the liquid from the body.

The liquid-sending-sucking dual-purpose tube 6 comprises a bulge section 61, a channel switching section 62, a liquid supply port 63 for connection to the liquid storage section 23, and a connection port 64 for connection to the catheter 3.

As described above, the bulge section 61 is a tube formed into a bag shape, and designed such that it expands or shrinks in accordance with the pressure in the tube. Thus, by detecting the amount of displacement of the bulge section 61 by the contact-type displacement gauge 221, the internal pressure of the catheter 3 connected to the liquid-sending-sucking dual-purpose tube 6 can be measured through the liquid-sending-sucking dual-purpose tube 6.

The channel switching section 62 in the first example is a three-way check valve 621, and connected to the primary side of the pump 21. Therefore, when the liquid is to be sent, forward rotation of the pump 21 switches the channel of the three-way check valve 621 to the direction in which the liquid storage section 23 is connected to the pump 21, allowing the liquid to flow to the catheter 3. Further, when the liquid is to be sucked from the catheter 3, reverse rotation of the pump 21 switches the channel of the three-way check valve 621 to the direction in which the pump 21 is connected to the waste liquid section 7, allowing the sucked liquid to be discharged to the waste liquid section 7.

The liquid supply port 63 may be in any form as long as the liquid can be supplied from the liquid storage section 23 into the liquid-sending-sucking dual-purpose tube 6. In the first example, since the liquid storage section 23 is an infusion bag, the liquid supply port 63 is preferably a needle 631 capable of piercing the infusion bag.

The connection port 64 may be in any form as long as it can be connected to the catheter 3. It is preferably a three-way stopcock. In this example, when malfunction of the in vivo temperature control system occurs, a syringe or the like can be connected to enable manual sending and sucking of the liquid.

The following describes a first control operation procedure that detects a spatial change in the esophagus by measuring the temperature changes in the longitudinal direction in the esophagus by injection of a liquid during treatment of arrhythmia by a catheter ablation procedure.

Step 1: Operation of Sending Liquid (Cooling Water) into Biological Lumen

To grasp the narrowed state or obstructed state in the esophagus 71 in advance, the operator operates the monitor 5 to perform liquid sending before the start of the catheter ablation procedure. Specifically, by operating the touch-screen display 51 on the monitor 5, a driving command regarding the liquid-sending rate and the liquid-sending time is outputted from the control section 24 to the pump 21 according to preset conditions, whereby a liquid 73 (cooling water) is sent from the liquid storage section 23 into the esophagus through the liquid-sending-sucking dual-purpose tube 6 and the catheter 3.

Apart from starting the liquid-sending operation by directly operating the touch-screen display 51 described above, the control section 24 may also start the liquid-sending operation when certain conditions are met such as the internal temperature of the esophagus 71 exceeding the threshold. In this example, after a catheter ablation procedure for ablation of the cardiac tissue begins in a position close to the left atrium, the internal temperature of the esophagus 71 gradually increases in the vicinity thereof, and the internal esophageal temperatures as measured by the temperature sensors 42 of the temperature probe 4 also gradually increase. In the control section 24, a threshold of the internal esophageal temperature at which the sending of the cooled liquid 73 (cooling water) is begun can be preliminarily set, and the process of comparing the temperature information of the temperature sensor 42 with the threshold is constantly carried out. When the temperature information detected by at least one of the temperature sensors 42 has reached the threshold, the control section 24 outputs a driving command regarding the liquid-sending rate and the liquid-sending time to the pump 21. As a result, the liquid 73 (cooling water) is sent from the liquid storage section 23 into the esophagus through the liquid-sending-sucking dual-purpose tube 6 and the catheter 3.

Step 2: Assessment of Temperature Change in Biological Lumen

The control section 24 determines whether or not there is any temperature change in the temperatures detected by all the temperature sensors 42 placed upstream to downstream in the flow direction of the liquid 73 before and after the liquid 73 is sent into the esophagus 71. In the first control operation procedure, the information on whether the temperature sensors 42 are positioned upstream or downstream in the flow direction of the liquid 73 is preset in the control section 24. By this, the control section 24 can judge the temperature changes in the flow direction of the liquid 73 without judgment on the positional information of the temperature sensors 42.

Figure 3:
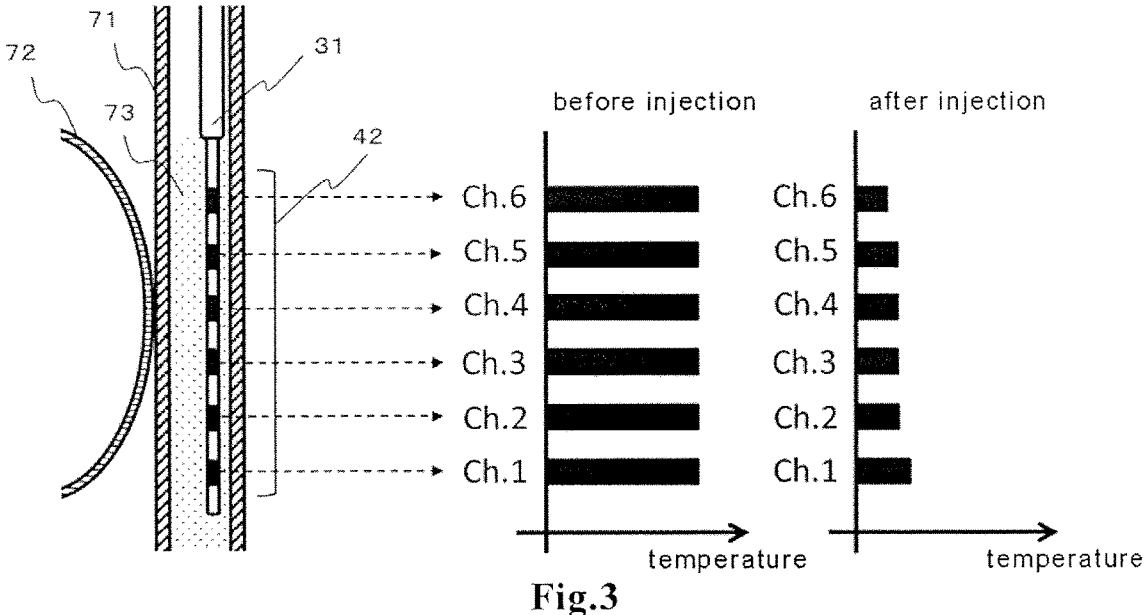
FIG. 3 is a schematic diagram illustrating temperature changes with time in the in vivo temperatures before and after injection of a liquid into a biological lumen in the first control operation of the in vivo temperature control system.

When temperature changes are observed in the temperatures in the esophagus 71 detected by all the temperature sensors 42 before and after the liquid 73 is sent into the esophagus 71, in other words, when the liquid 73 smoothly flows down from upstream to downstream to lower the temperature of the esophagus 71, then the control section 24 judges that the inside of the esophagus 71 is not in a narrowed state or obstructed state. For example, as described in FIG. 3, when, in the temperatures in the esophagus 71 detected by all the temperature sensors 42 (Ch. 1 to Ch6) in the temperature probe 41 inserted into the esophagus 71, temperature changes larger than a preset threshold by injection of the liquid 73 are detected, then the control section 24 judges that the esophagus 71 is not in a narrowed state or obstructed state. Specifically, for example, when the temperature in the esophagus 71 is about 37° C., and the temperature changes in the esophagus 71 detected by all the temperature sensors 42 are 3° C./sec or more, then the control section 24 preferably judges that the esophagus 71 is not in a narrowed state or obstructed state.

Figure 4:
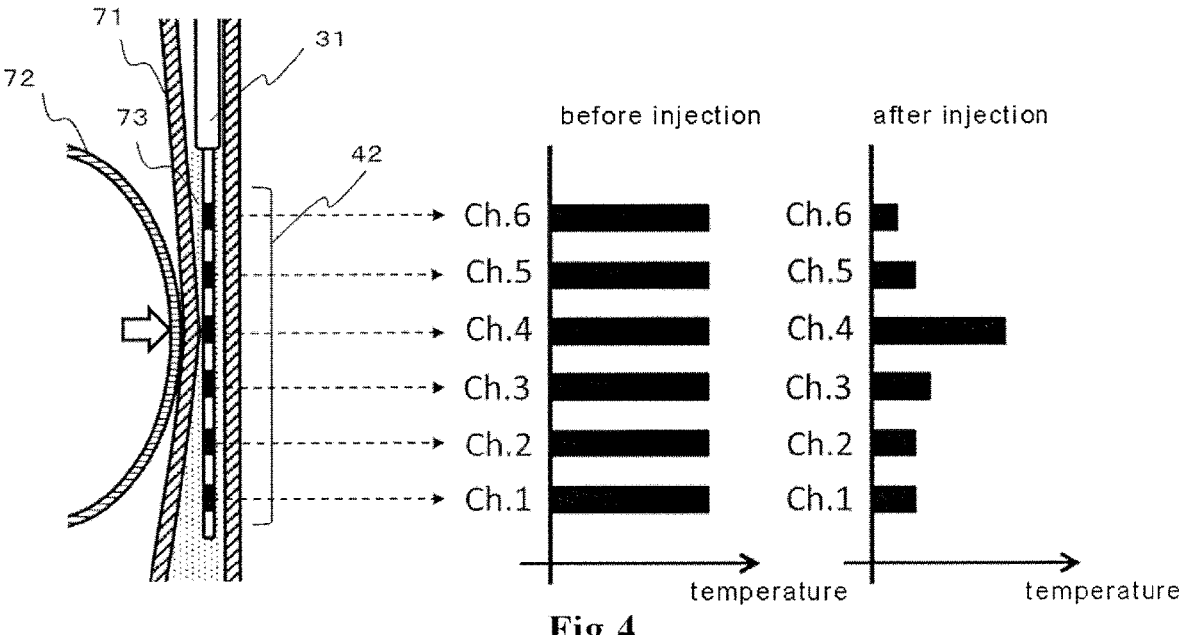
FIG. 4 is a schematic diagram illustrating temperature changes with time in the in vivo temperatures before and after injection of a liquid into a biological lumen in a narrowed state in the first control operation of the in vivo temperature control system.

On the other hand, when any one of the temperature sensors 42 positioned upstream in the flowing direction of the liquid 73 showed a temperature change, and a temperature sensor 42 positioned downstream in the flowing direction of the liquid 73 showed a temperature change, and a temperature change detected by a temperature sensor 42 positioned between the temperature sensor 42 positioned upstream and the temperature sensor 42 downstream is smaller than a preset threshold, then the control section 24 judges that the esophagus 71 is in a narrowed state. Specifically, for example, when the temperature in the esophagus 71 is about 37° C., and as shown in FIG. 4, where the temperature changes in the esophagus 71 detected by the temperature sensors 42 (Ch. 5, Ch. 6) positioned upstream and the temperature sensors 42 (Ch. 1 to Ch. 3) positioned downstream in the flowing direction of the liquid 73 are 3° C./sec or more, and the temperature change in the esophagus detected by the temperature sensor 42 (Ch. 4) positioned between the temperature sensors positioned upstream and the temperature sensors 42 positioned downstream is from 0 to 3° C./sec, then the control section 24 preferably judges that the esophagus 71 is in a narrowed state because of compression by the cardiac muscle tissue 72.

Figure 5:
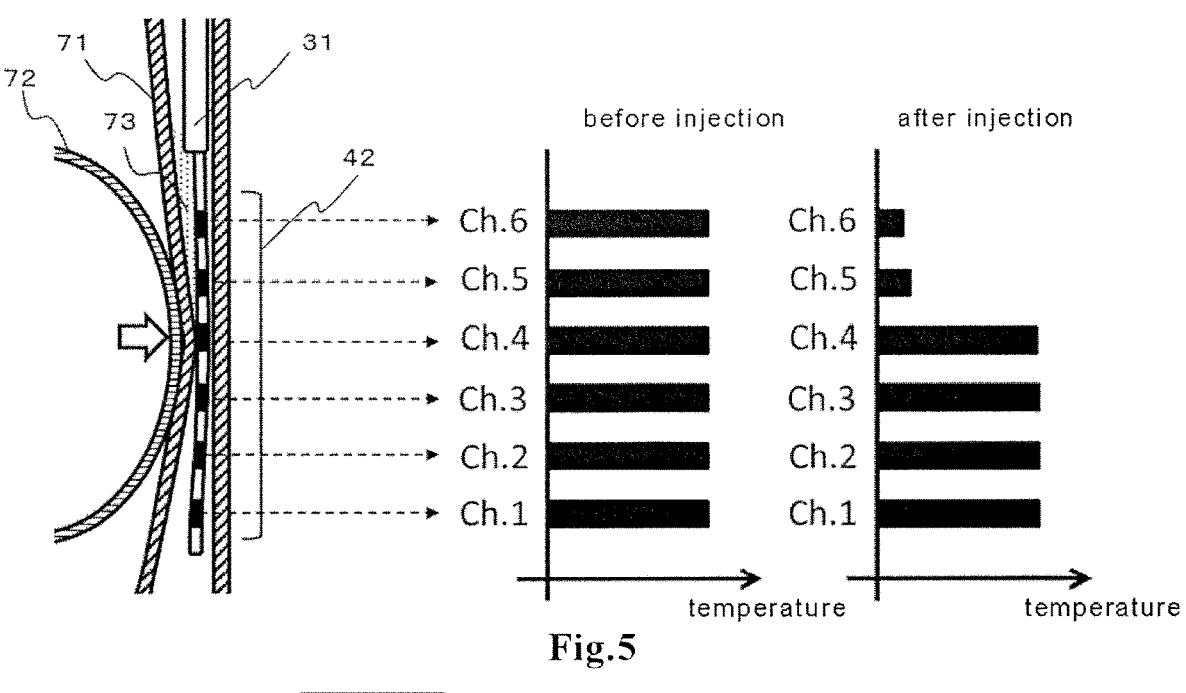
FIG. 5 is a schematic diagram illustrating temperature changes with time in the in vivo temperatures before and after injection of a liquid into a biological lumen in an obstructed state in the first control operation of the in vivo temperature control system.

When the temperature change detected by any one of the temperature sensors 42 positioned upstream in the flowing direction of the liquid 73 is smaller than a preset threshold, and temperature changes in the esophagus detected by all temperature sensors 42 positioned downstream, in the flowing direction of the liquid 73, of the temperature sensor 42 detecting the temperature change smaller than a threshold are smaller than a preset threshold, then it is judged that the esophagus 71 is in an obstructed state. Specifically, for example, when the temperature in the esophagus 71 is about 37° C., and as shown in FIG. 5, the temperature changes in the temperatures inside the esophagus 71 detected by the temperature sensors (Ch. 5, Ch. 6) positioned upstream are 3° C./sec or more, and the temperature changes in the temperature inside the esophagus detected by the temperature sensors 42 (Ch. 1 to Ch. 4) positioned downstream are from 0 to 3° C./sec, then the control section 24 preferably judges that the esophagus 71 is in an obstructed state because of compression by the cardiac muscle tissue 72.

Step 3: Alerting to Operator

When there is a spatial change in a biological lumen, in other words, when the esophagus 71 is judged to be in a narrowed state or obstructed state, the control section 24 transmits the judgment result to the operator by visual means or aural means. Specifically, the control section 24 can transmit the judgment result by displaying on the monitor 5 the fact that the esophagus is in a narrowed state or obstructed state as a visual information toward the operator, or allowing the alert output section to generate an alert such as alarm.

Figure 6:
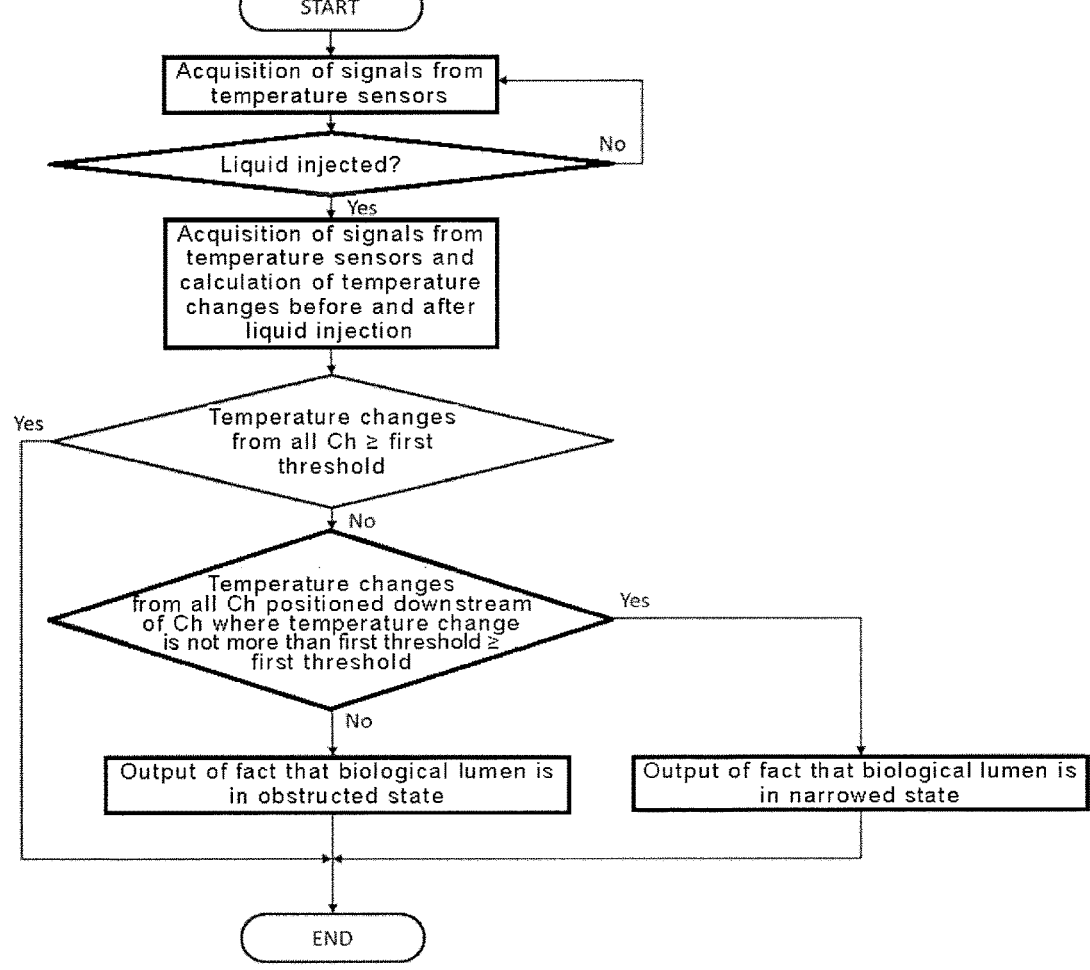
FIG. 6 is a flow chart illustrating an operational procedure of the control section in the first control operation in the in vivo temperature control system.

A flow chart illustrating an example of the operational procedure for the control section 24 in the first control method is described below using FIG. 6.

In this example of the operational procedure, the control section 24 first detects a signal(s) (such as the thermoelectromotive force) from the temperature sensor(s) 42 in the temperature probe 4 connected to the in vivo temperature control device 2, and then converts the signal(s) to temperature information (in vivo temperature(s)). Thereafter, average temperature per unit time is calculated based on the temperature measurement data.

Next, the control section 24 judges whether or not there has been liquid sending into the biological lumen. When there has been liquid sending, temperature changes from the instantaneous values or the average values of the in vivo temperatures before the liquid sending to the in vivo temperatures detected by the plurality of temperature sensors 42 after the liquid sending are determined. Then, it is judged whether or not the temperatures in the biological lumen obtained by the temperature sensors 42 show temperature changes larger than a preset threshold (first threshold). When all the temperature sensors 42 detect temperature changes larger than the preset threshold, the control section 24 judges that the inside of the biological lumen is not in a narrowed state or obstructed state.

On the other hand, when a temperature sensor 42 detects a temperature change smaller than a preset threshold (first threshold), then the control section 24 makes a judgment based on whether or not temperature changes larger than the preset threshold (first threshold) are detected by all the temperature sensors 42 positioned downstream, in the flowing direction of the liquid, of the temperature sensor 42 detecting the temperature change smaller than the threshold. When temperature changes larger than the preset threshold are detected by all the temperature sensors 42 positioned downstream in the flowing direction of the liquid, the control section 24 judges that the inside of the biological lumen is in a narrowed state. Conversely, when temperature changes larger than a preset threshold are not detected by all the temperature sensors 42 positioned downstream in the flowing direction of the liquid, the control section 24 judges that the inside of the biological lumen is in an obstructed state.

When temperature changes smaller than a preset threshold (first threshold) are detected by the plurality of temperature sensors 42, then the control section 24 may make a judgment based on, when the temperature sensor 42 positioned most downstream in the flowing direction of the liquid is considered as a starting point, whether or not temperature changes larger than the preset threshold are detected by all the temperature sensors 42 positioned downstream, in the flowing direction of the liquid, of the temperature sensor 42 as the starting point. When temperature changes larger than the preset threshold are detected by all the temperature sensors 42 positioned downstream, in the flowing direction of the liquid, of the temperature sensor 42 as the starting point, the control section 24 judges that the inside of the biological lumen is in a narrowed state. Conversely, when temperature changes larger than the preset threshold are not detected by all the temperature sensors 42 positioned downstream, in the flowing direction of the liquid, of the temperature sensor 42 as the starting point, the control section 24 judges that the inside of the biological lumen is in an obstructed state.

When temperature changes larger than a preset threshold (first threshold) are not detected by all the temperature sensors 42, the control section 24 judges that the inside of the biological lumen is in an obstructed state.

When the control section judges that the inside of the biological lumen is in a narrowed state or obstructed state, the control section displays on the monitor 5 the fact that the inside of the biological lumen is in a narrowed state or obstructed state as visual information, or allows the alert output section to generate an alert such as alarm.

INDUSTRIAL APPLICABILITY

Our systems can be applied in medical fields in which detection of temperature rising or cooling in a biological lumen is required, and is particularly applicable to when the temperature raised during catheter ablation procedure is cooled.

The invention claimed is:

1. An in vivo temperature control system comprising:
a catheter insertable into a biological lumen;
two or more temperature sensors placed such that they can measure a temperature distribution in a longitudinal direction of the biological lumen;
a liquid storage section that stores a liquid; and
a control section that estimates a spatial change in the biological lumen based on a temperature change before and after the liquid in the liquid storage section is released outwardly through the catheter,
wherein the temperature change is measured by each of the two or more temperature sensors;
wherein the spatial change is a narrowed state or obstructed state of the biological lumen;
wherein, in estimating the spatial change in the biological lumen, the control section judges that the biological lumen is not in the narrowed state or obstructed state when temperature changes larger than a preset threshold are detected by all of the two or more temperature sensors.

2. The in vivo temperature control system of claim 1, further comprising a monitor that displays signals detected by the temperature sensors, as a visual information,
wherein the monitor allows an operator to know the spatial change in the biological lumen.

3. An in vivo temperature control system comprising:
a catheter insertable into a biological lumen;
two or more temperature sensors placed such that they can measure a temperature distribution in a longitudinal direction of the biological lumen;
a liquid storage section that stores a liquid; and
a control section that estimates a spatial change in the biological lumen based on a temperature change before and after the liquid in the liquid storage section is released outwardly through the catheter,
wherein the temperature change is measured by each of the two or more temperature sensors;
wherein the spatial change is a narrowed state or obstructed state of the biological lumen;
wherein, in estimating the spatial change in the biological lumen, the control section judges that the biological lumen is in the narrowed state or obstructed state based on, in the temperature changes in the longitudinal direction of the biological lumen detected by the two or more temperature sensors, whether a temperature change smaller than a preset threshold is detected by any one of the temperature sensors, and temperature changes larger than the preset threshold are detected by all the temperature sensors positioned downstream, in the flowing direction of the liquid, of the temperature sensor that detects the temperature change smaller than the threshold.

4. An in vivo temperature control system comprising:

a catheter insertable into a biological lumen;

two or more temperature sensors placed such that they can measure a temperature distribution in a longitudinal direction of the biological lumen;

a liquid storage section that stores a liquid; and a control section that estimates a spatial change in the biological lumen based on a temperature change before and after the liquid in the liquid storage section is released outwardly through the catheter, wherein the temperature change is measured by each of the two or more temperature sensors;

wherein the spatial change is a narrowed state or obstructed state of the biological lumen;

comprising an alert output section that outputs an alert when the biological lumen is judged to be in the narrowed state or obstructed state;

wherein, in estimating the spatial change in the biological lumen, the control section judges that the biological lumen is not in the narrowed state or obstructed state when temperature changes larger than a preset threshold are detected by all the two or more temperature sensors.

5. An in vivo temperature control system comprising:

a catheter insertable into a biological lumen;

two or more temperature sensors placed such that they can measure a temperature distribution in a longitudinal direction of the biological lumen;

a liquid storage section that stores a liquid; and a control section that estimates a spatial change in the biological lumen based on a temperature change before and after the liquid in the liquid storage section is released outwardly through the catheter, wherein the temperature change is measured by each of the two or more temperature sensors;

wherein the spatial change is a narrowed state or obstructed state of the biological lumen; comprising an alert output section that outputs an alert when the biological lumen is judged to be in the narrowed state or obstructed state;

wherein, in estimating the spatial change in the biological lumen, the control section judges that the biological lumen is in the narrowed state or obstructed state based on, in the temperature changes in the longitudinal direction of the biological lumen detected by the two or more temperature sensors, whether a temperature change smaller than a preset threshold is detected by any one of the temperature sensors, and temperature changes larger than the preset threshold are detected by all the temperature sensors positioned downstream, in the flowing direction of the liquid, of the temperature sensor that detects the temperature change smaller than the threshold.

\*    \*    \*    \*    \*